(12) United States Patent
Ogawa

(10) Patent No.: US 6,934,590 B2
(45) Date of Patent: Aug. 23, 2005

(54) QUALITY CONTROL SYSTEM FOR MEDICAL DIAGNOSTIC APPARATUS

(75) Inventor: Eiji Ogawa, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/536,315

(22) Filed: Mar. 27, 2000

(65) Prior Publication Data
US 2003/0153814 A1 Aug. 14, 2003

(30) Foreign Application Priority Data
Mar. 25, 1999 (JP) .......... 11-082023

(51) Int. Cl.7 .............. G05B 11/01
(52) U.S. Cl. .............. 700/19; 700/20; 700/79
(58) Field of Search .............. 700/19–20, 79, 700/9, 21, 54; 382/132, 254, 312, 309, 318, 131; 378/196–197, 4, 8, 19–20; 600/524, 483, 300–301, 545–555; 709/203, 223–226, 201, 208, 220, 228; 345/660; 702/182, 185; 340/3.1

(56) References Cited

U.S. PATENT DOCUMENTS

| | | | |
|---|---|---|---|
| 5,365,310 A | * | 11/1994 | Jenkins et al. .......... 399/8 |
| 5,400,792 A | * | 3/1995 | Hoebel et al. .......... 600/483 |
| 5,600,574 A | * | 2/1997 | Reitan .......... 702/185 |
| 5,655,084 A | * | 8/1997 | Pinsky et al. .......... 705/3 |
| 5,786,994 A | * | 7/1998 | Friz et al. .......... 700/79 |
| 5,883,985 A | * | 3/1999 | Pourjavid .......... 382/274 |
| 6,381,348 B2 | * | 4/2002 | Takeo .......... 382/128 |
| 6,381,557 B1 | * | 4/2002 | Babula et al. .......... 702/183 |
| 6,418,334 B1 | * | 7/2002 | Unger et al. .......... 600/407 |
| 6,487,513 B1 | * | 11/2002 | Eastvold et al. .......... 702/108 |

* cited by examiner

Primary Examiner—Anthony Knight
Assistant Examiner—Ronald D Hartman, Jr.
(74) Attorney, Agent, or Firm—Sughrue Mion, PLLC

(57) ABSTRACT

The quality control system includes a network, a plurality of medical diagnostic apparatuses which exist on the network and have respective histories of evaluation results on specific items regarding quality of individual medical diagnostic apparatuses and a control device which exists on the network, stores all of the histories of the evaluation results that individual medical diagnostic apparatuses hold and controls them centrally. By this unified quality control system, quality control of a plurality of medical diagnostic apparatuses connected to each other on the network can efficiently be performed.

37 Claims, 3 Drawing Sheets

QUALITY CONTROL SYSTEM FOR MEDICAL DIAGNOSTIC APPARATUS

BACKGROUND OF THE INVENTION

The present invention relates to a quality control system for a plurality of medical diagnostic apparatuses existing on a network. More particularly, the present invention relates to a quality control system for controlling centrally image qualities of medical diagnostic apparatuses including image input devices and image output devices for medical diagnostic applications.

Various diagnostic apparatuses have heretofore been used in the medical field employing X-rays and other radiations. In radiology, X-rays passing through an object are detected and an image is generated for diagnostic purposes. Images taken by chest radiography have been used widely for quite many years.

Apparatuses relying upon CR (computerized radiography), CT (computerized tomography) and MRI (magnetic resonance imaging) are in commercial use. The images generated by these apparatuses are either displayed on CRT (cathode ray tube) displays or outputted on films by LP (laser printers) or the like for subsequent use in medical working fields to diagnose diseases.

Radiographic and other medical diagnostic apparatuses are making progressive shift toward digitizing. By the "digitizing" is meant a process in which the X-ray signal passing through an object is converted to a digital signal, which is appropriately processed to generate an image suitable for diagnosis.

In line with the highly advanced technologies of communications and computers of recent years, a network utilizing computers has been constructed within a hospital by connecting various medical diagnostic apparatuses described above onto the network.

In the apparatus for CR, there is used a stimulable phosphor which, upon irradiation with a radiation, accumulates part of its energy and upon illumination with exciting light such as visible light or laser light, produces stimulated light emission in accordance with the accumulated radiation energy. The radiation image information about an object such as the human body or the like is first recorded in a sheet of stimulable phosphor (commonly called as "a stimulable phosphor sheet"), which is then scanned with exciting light such as laser light or the like to produce stimulated light which is read photoelectrically as an electric signal, producing an image signal.

When CR is connected to the above-described network, such radiation image recording and reading system may not be connected to the network in its entirety but only an image reading device which reads an image recorded in the stimulable phosphor sheet may be connected to the network thereby inputting the image signal into the network.

In order to prevent a wrong diagnosis, the above-described medical diagnostic apparatuses are required to have a strict display performance; thus, quality control of these medical diagnostic apparatuses is important.

For example, performance of the image reading device to read the X-ray radiograph is characterized by sensitivity, granularity, S/N (signal to noise ratio) or the like. The quality of the image reading device as to what performance the device has can be checked by comparing a relationship between characteristic values (such as RMS (Root Mean Square), DQE (Detective Quantum Efficiency) or the like) computed from the image data obtained by reading the stimulative phosphor sheet on which an image was recorded with X-ray in radiation and X-ray radiation dose to be illuminated on the stimulative phosphor sheet, with the predetermined values which have preliminarily been set.

Moreover, the quality (image quality of a displayed image such as a brightness and resolution characteristics or the like) of a soft copy display device (output device) such as CRT, LCD or the like can be checked by a visual evaluation employing a test pattern or the like such as SMPTE pattern which can check various image qualities comprehensively. However, the qualities of medical diagnostic apparatuses have conventionally been checked individually such that the image quality is checked every time the image quality test is performed, for example, when represents one of the qualities of medical diagnostic apparatuses; and image qualities of a plurality of medical diagnostic apparatuses connected onto the network have not been controlled as a whole.

Therefore, in an institution, such as a large hospital, where a number of medical diagnostic apparatuses are installed, though there has been a necessity for controlling qualities of apparatuses such as image quality level and the like of an image input device (reading device), an image output device (display device) and the like as a whole, respective devices only hold respective results of quality checks individually. In other words, efficiency has been very low in the conventional quality control.

SUMMARY OF THE INVENTION

The present invention has been accomplished under these circumstances and has an object to provide a quality control system for medical diagnostic apparatus that is capable of performing efficient quality control of a plurality of medical diagnostic apparatuses connected onto a network.

In order to solve the aforementioned problems, a first aspect of the present invention provides a quality control system for medical diagnostic apparatus, comprising a plurality of medical diagnostic apparatuses having respective histories of evaluation results on specified items regarding quality of individual medical diagnostic apparatuses, a control device which stores all of the histories of the evaluation results which respective medical diagnostic apparatuses hold to control the histories thereof centrally and a network onto which the plurality of medical diagnostic apparatuses and the control device are connected.

In other words, a quality control system of the present invention for a plurality of medical diagnostic apparatuses existing on a network comprises a control device on the network, wherein respective medical diagnostic apparatuses hold respective histories of evaluation results on specified items regarding quality of respective medical diagnostic apparatuses, and wherein the control device stores all of the histories of the evaluation results which respective medical diagnostic apparatuses hold to control the histories centrally.

In order to solve the aforementioned problems, a second aspect of the present invention provides a quality control system for medical diagnostic apparatus, comprising a plurality of medical diagnostic apparatuses, a control device which stores all of histories of evaluation results on specified items regarding quality of individual medical diagnostic apparatuses to control the histories thereof centrally and a network onto which the plurality of medical diagnostic apparatuses and the control device are connected. In other words, a quality control system of the invention for a plurality of medical diagnostic apparatuses existing on a network comprises a control device on the network, wherein the control device stores all of histories of evaluation results on specified items regarding quality of respective medical diagnostic apparatuses as a whole to control the histories centrally.

Moreover, each of the plurality of medical diagnostic apparatuses preferably comprises at least one of a medical image input device or a medical image output device.

BRIEF DESRIPTION OF THE DRAWINGS

DETAILED DESCRIPTION OF THE INVENTION

A quality control system of medical diagnostic apparatus in accordance with the present invention is described below in detail with reference to the preferred embodiments shown in the accompanying drawings.

Figure 1:
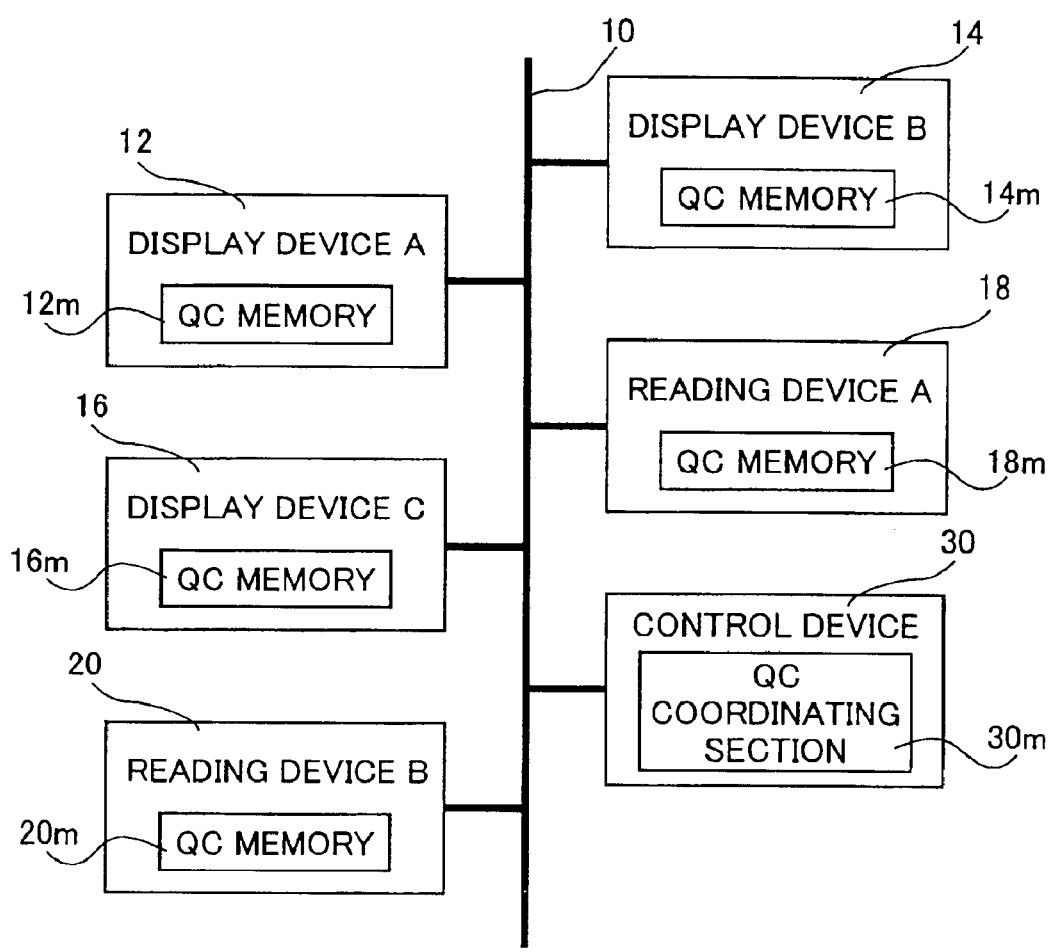
FIG. 1 is a block diagram showing schematically a quality control system of medical diagnostic apparatus according to a first embodiment of the present invention.

FIG. 1 is a block diagram showing schematically a quality control system of medial diagnostic apparatus according to a first embodiment of the present invention.

The present embodiment is a quality control system that centrally controls qualities of a number of medical diagnostic apparatuses connected onto a network in a medical institution such as a hospital or the like. "Quality" in this case is meant by quality of an image which is important particularly in medical diagnosis. Therefore, the medical diagnostic apparatuses in consideration here are those which are concerned with an image quality problem. Such apparatuses which are concerned with the image quality problem include an image input device (reading device) and an image output device (display device).

FIG. 1 shows a portion of the above-described quality control system of the invention, that is, a network system.

As shown in FIG. 1, connected to a bus 10 are a number of medical diagnostic apparatuses, namely, a display device A12, a display device B14, a display device C16, a reading device A18, a reading device B20, and so forth, as well as a control device 30 for coordinating QC (quality control, here image quality control) results of these devices.

Devices 12, 14, 16, 18 and 20 have QC memories 12m, 14m, 16m, 18m and 20m, respectively, as storing sections for storing respective QC results. The control device has a QC coordinating section 30m for coordinating and storing all of the QC results of respective devices.

A method of checking the image quality of each device (12–20) will be described below.

The image quality check may be performed automatically or manually with a unit particularly arranged for the purpose of the image quality check. Moreover, such particular unit for the image quality check may be attached to each device (12–20) or be a portable testing instrument as a separate type to be only put in use at the time of the image quality check. When the image quality check is performed automatically with the particular unit, the result of the image quality check (QC result) is automatically stored in the QC memory (12m–20m) of each device, whereas, when the image quality check is performed manually, the result is manually inputted by means of a keyboard or the like connected to each device (12–20).

First of all, since characteristic values involving linearity (relationship between exposed X-ray radiation dose onto a stimulable phosphor sheet and light emission quantity from it), values of granularity such as RMS or the like, S/N ratio such as DQE or the like are in close relationships with the exposed X-ray dose, the image quality check of a reading device is performed by computing such relationships. An example of such image quality check of the reading device (18, 20) is described below but the image quality check is by no means limited to this particular example.

At first, at the time a reading device (18, 20) is installed, a stimulable phosphor sheet irradiated preliminarily with a predetermined dose of radiation is read to obtain image data; then characteristic values are computed from the thus obtained image data; thereafter relationships between the above-described dose and the computed characteristic values are stored. After a certain period of time has passed, the stimulable phosphor sheet irradiated with the X-ray radiation again in the same manner as above is read to obtain image data; then the above-described characteristic values are computed from the thus obtained image data to obtain relationships with the radiation dose; thereafter these newly obtained relationships and the above-described relationships between the radiation dose and the characteristic values which have preliminarily been computed and stored are compared with each other to check the image quality (device performance) of the reading device (18 or 20) of interest.

Next, the image quality check of each display device (12, 14 or 16) is performed, for example, by actually displaying an image and then checking brightness, sharpness, granularity or the like of the thus displayed image. An example of image quality checking method of the display device (12, 14, 16) is described below but the method is of course not limited to this particular example.

For example, at the time of device installation, a predetermined test pattern is displayed on a display device (12, 14, 16); then the displayed test pattern is taken with an appropriate an image pickup device to obtain image data; thereafter the thus obtained image data is stored. After a certain period of time has passed, the above-described test pattern is displayed again to obtain the image data in the same manner as above; then the newly obtained image data and the image data preliminarily stored are compared with each other. A shift or the like between them is computed to obtain a change of the image quantitatively thereby checking the image quality.

As an alternative, as has been performed conventionally, a test pattern such as SMPTE pattern or the like may be displayed to check the image quality by human eyes.

The QC result of the image check of each device (12–20) is stored in a memory (12m–20m) in each device (12–20). When the image quality is checked by human eyes, the QC result may be inputted manually via keyboard or the like connected to the device (12–20) of interest.

Next, the control device 30 issues an request for the QC result to each device (12–20) connected onto the network. At such order, each device (12–20) outputs the QC result stored in a storing section in each device (12–20) to the control device 30. The control device 30 stores the QC results of all the devices (12–20) in the storing section, namely, the QC coordinating section 30m in the control device 30.

The control device 30 displays the QC result of each device (12–20) categorized in accordance with items or objects if necessary. In the control device 30, a method of displaying the QC result can be designated by means of an inputting unit such as the keyboard or the like connected to the control device 30.

Figure 2A:
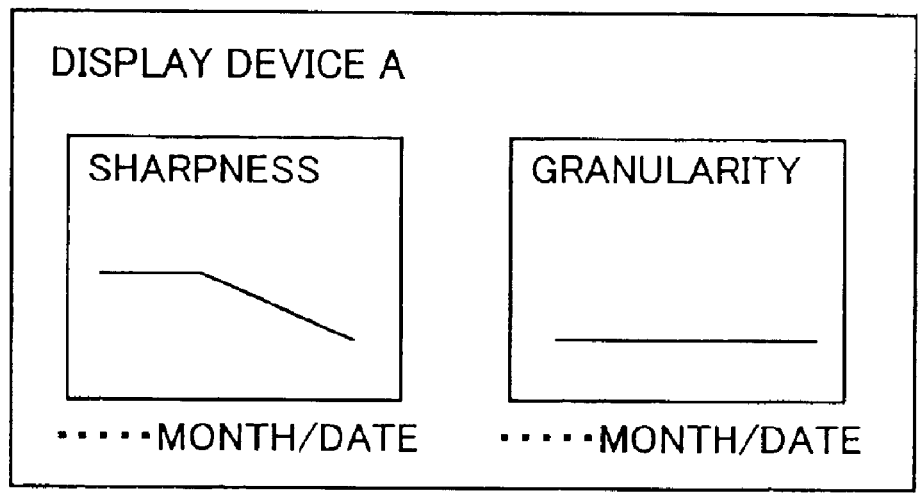
FIG. 2A illustrates an example of QC result held by a display device A and FIG. 2B illustrates an example of QC result held by a display device B.
Figure 2B:
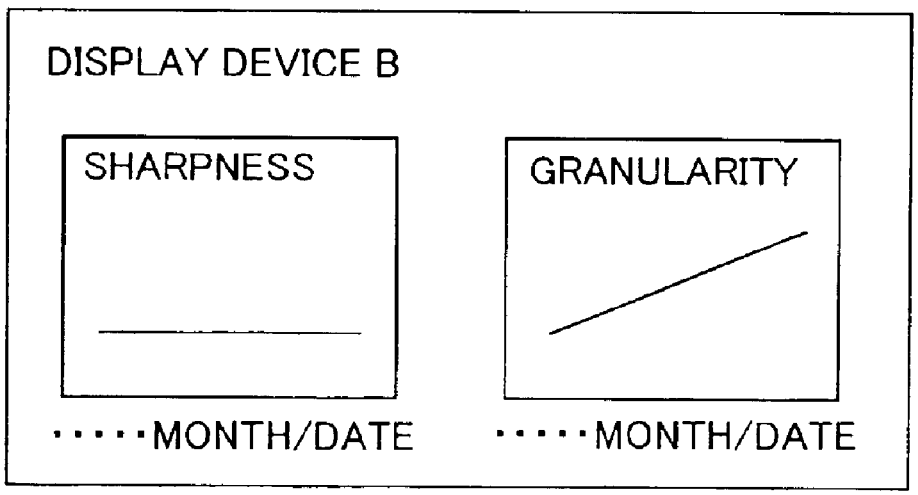

FIG. 2 illustrates an example of QC result held by each device (12–20). FIG. 2A is an example of QC result held by the QC memory 12m of the display device A12, whereas FIG. 2B is an example of QC result held by the QC memory 14m of the display device B14. As shown in FIGS. 2A and 2B, each device (12–20) holds the QC result as data showing changes with the passage of time, namely, the history of the QC result on an item basis, such as sharpness, granularity or the like.

According to FIG. 2A, it can be mentioned that the image quality of the display device A12 have scarcely been changed in granularity but has gradually been deteriorated in sharpness with the passage of time. On the other hand, according to FIG. 2B, it is known that the image quality of the display device B14 has scarcely been changed in sharpness but has been deteriorated in granularity with the passage of time.

Figure 3:
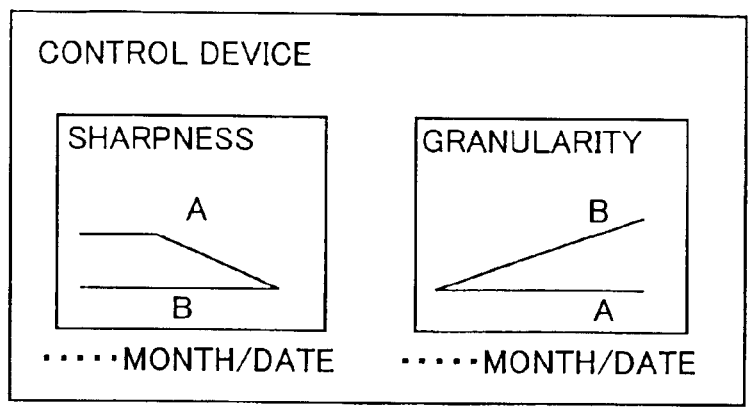
FIG. 3 illustrates a display example of QC result held by a control device.

An example of display of the QC result of each device (12–20) held by the QC coordinating section 30m of the control device 30 is shown in FIG. 3. In FIG. 3, sharpness and granularity are taken as items. In the example shown in FIG. 3, the control device 30 displays changes with the passage of time of each item in each device (12–20). In FIG. 3, only two devices (display devices A12 and B14) are displayed for simplicity purposes but, in practice, it is capable of displaying the QC results of all devices connected onto the network.

Therefore, once the control device 30 is viewed, the QC results of all devices (12–20) can be obtained instantly; thus, the present status of each device (12–20) according to the difference of the installation position, usage condition or the like can be accurately obtained.

A second embodiment of the present invention will subsequently be described.

Figure 4:
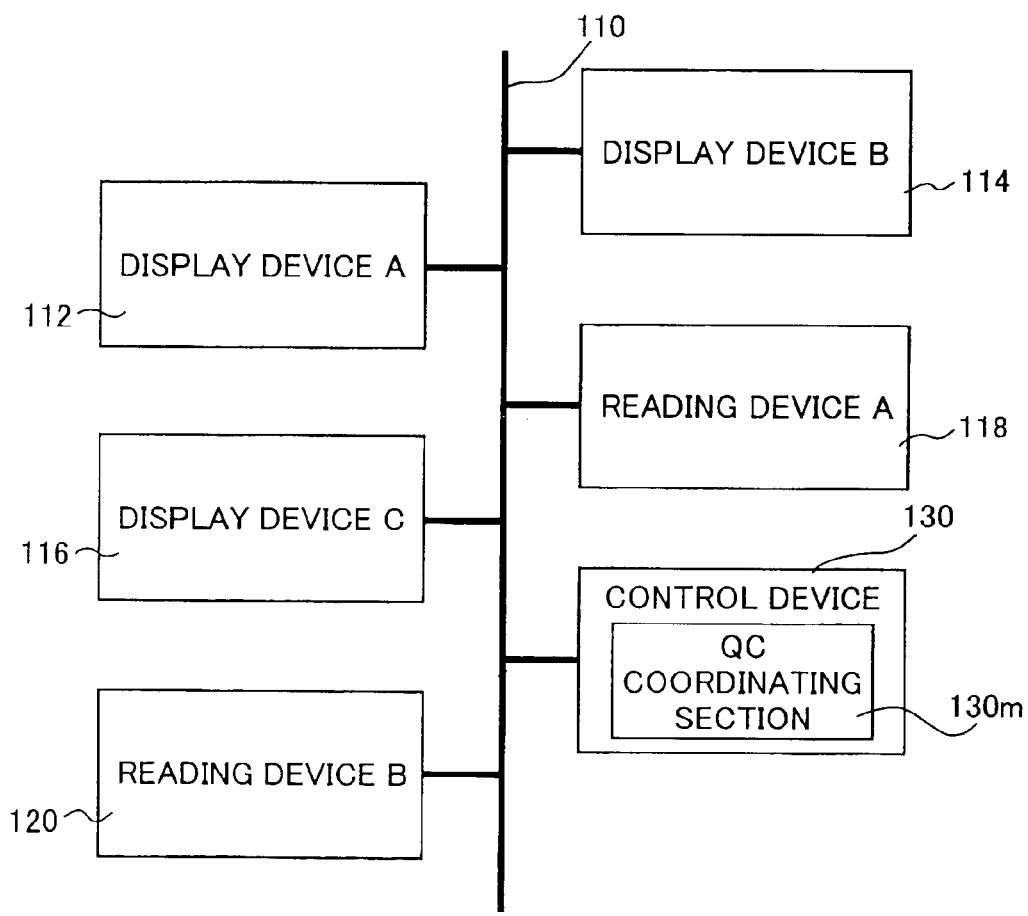
FIG. 4 is a block diagram showing schematically a quality control system of medical diagnostic apparatus in accordance with a second embodiment of the present invention.

In the same way as in the first embodiment, the second embodiment is a quality control system that controls qualities of a number of medical diagnostic apparatuses connected onto a network centrally in a medical institution such as a hospital or the like. The present embodiment differs from the first embodiment in that each device does not have a memory to store a quality result therein and, instead, the control device coordinates all the QC results and then stores the thus coordinated QC results therein. In FIG. 4, a quality control system of medical diagnostic apparatus of the present embodiment is schematically shown.

As is shown in FIG. 4, connected to a bus 110 are a number of devices, such as a display device A112, a display device B114, a display device C116, a reading device A118, a reading device B120 and so forth, and a control device 130.

None of individual devices (112, 114, 116, 118 or 120) has a memory to store the QC result therein and, instead, the control device 130 has a QC coordinating section 130m which is a memory for holding the QC results of all devices (112–120).

A method of checking the image quality of each device (112–120) is similar to that of the first embodiment.

The QC result of each device (112–120) is immediately outputted to the control device 130 without waiting for a request from the control device 130; then the QC results of all devices (112–120) are coordinated and stored in the QC coordinating section 130m in the control device 130.

The QC results are shown in the control device 130 in a similar form as shown in FIG. 3. These QC results can be retrieved from the control device 130 by respective devices (112–120) for viewing them and, if needed, only a history part of the QC result related to each device (112–120) can be viewed.

As such, the control device 130 coordinates and controls centrally all of the QC results of respective devices (112–120) so that the quality control of respective devices (112–120) on the network can be performed with a high efficiency. Since even a small deterioration in quality of the displayed image for use in a medical diagnosis can lead to a wrong diagnosis, the image with a high precision is required. Since the quality control is very important, the quality of the image produced by the medical diagnostic apparatus is sufficiently enhanced in a consistent manner by performing a central (unified) quality control as described above.

For example, in a large hospital, medical diagnostic devices are installed in various positions for using them exclusively in respective positions. As long as the image of only one device is viewed, it is difficult to recognize the changes with the passage of time of the image quality of each device.

However, once the QC results are coordinated in one place and controlled centrally as described above, the changes with the passage of time of the image quality of each device can be obtained through comparison with those of a number of other devices. In this case, if there is any device the image of which is extremely deteriorated, it is easy to investigate the cause of such deterioration and then to take a countermeasure.

In each of the above-described embodiments, the control device (30 or 130) for exclusive use is provided for controlling the quality results centrally. However, the control device is not necessary to be of such exclusive type but one of devices which have been connected onto the network may be utilized as the control device.

While the quality control system of the medical diagnostic apparatus of the present invention has been described above in detail, it should be noted that the present invention is by no means limited to the foregoing examples and that various improvements and modifications can of course be made without departing from the scope and spirit of the present invention.

As described on the foregoing pages, according to the present invention, the quality of each medical diagnostic device connected onto the network can be controlled centrally so that it has become capable of controlling the quality of each device efficiently.

What is claimed is:

1. A quality control system for medical diagnostic apparatuses, wherein said medical diagnostic apparatuses comprise at least one medical image input device, said quality control system comprising:

a plurality of medical image input devices holding respective histories of evaluation results on specified items regarding image quality of individual medical image input devices;

a control device which stores all of the histories of said evaluation results regarding the image quality which respective medical image input devices hold to control the histories thereof centrally; and a network onto which said plurality of medical image input devices and said control device are connected.

2. The quality control system according to claim 1, wherein said medical diagnostic apparatuses comprise at least one medical image output device that is connected onto said network.

3. The quality control system according to claim 2, wherein said at least one medical image output device has a history of evaluation results related to its quality and said control device stores the history of evaluation results related to quality of said at least one medical output device, to control the history thereof centrally.

4. The quality control system according to claim 2, wherein said at least one medical image output device includes a soft copy display device.

5. The quality control system according to claim 2, wherein said at least one medical image output device stores therein said history of evaluation results related to a quality of said at least one medical image output device.

6. The quality control system according to claim 1, further comprising a portable testing unit for performing an image quality check.

7. The quality control system according to claim 1, wherein at least one of said plurality of medical diagnostic apparatuses is said control device.

8. The quality control system according to claim 7, further comprising a portable testing unit for performing an image quality check.

9. The quality control system according to claim 1, wherein said image quality includes at least one of sensitivity, granularity, root mean square (RMS), detective quantum efficiency (DQE), brightness characteristic of a soft copy display device and resolution characteristic of the soft copy display device.

10. The quality control system according to claim 1, wherein said quality control system is applied to a computerized radiography (CR) imaging system.

11. The quality control system according to claim 1, wherein at least one of said plurality of medical image input devices originates an image from a source being imaged using energy conversion to an electrical signal.

12. The quality control system according to claim 1, wherein at least one of said plurality of medical image input devices is selected from one of a computerized radiography (CR) device, a computerized tomography (CT) device, and a magnetic resonance imaging (MRI) device.

13. The quality control system according to claim 1, wherein said histories of evaluation results are multiple data entries over time.

14. A quality control system for medical diagnostic apparatuses, wherein said medical diagnostic apparatuses comprise at least one medical image input device, said quality control system comprising:
   a plurality of medical image input devices;
   a control device which stores all histories of evaluation results on specified items regarding image quality of individual medical image input devices to control the histories thereof centrally; and
   a network onto which said plurality of medical image input devices and said control device are connected.

15. The quality control system according to claim 14, wherein said medical diagnostic apparatuses comprise at least one medical image output device that is connected onto said network.

16. The quality control system according to claim 15, wherein said control device also scores a history of evaluation results related to quality of said at least one medical output device, to control the history thereof centrally.

17. The quality control system according to claim 15, wherein said at least one medical image output device includes a soft copy display device.

18. The quality control system according to claim 14, further comprising a portable testing unit for performing an image quality check.

19. The quality control system according to claim 14, wherein said at least one of said plurality of medical diagnostic apparatuses immediately outputs said history of evaluation results on specified items regarding quality of at least one of said plurality of medical diagnostic apparatuses, after determining said history.

20. The quality control system according to claim 14, wherein said image quality includes at least one of sensitivity, granularity, root mean square (RMS), detective quantum efficiency (DQE), brightness characteristic of a soft copy display device and resolution characteristic of the soft copy display device.

21. The quality control system according to claim 14, wherein said quality control system is applied to a computerized radiography (CR) imaging system.

22. The quality control system according to claim 14, wherein at least one of said plurality of medical image input devices originates an image from a source being imaged using energy conversion to an electrical signal.

23. The quality control system according to claim 14, wherein at least one of said plurality of medical image input devices is selected from one of a computerized radiography (CR) device, a computerized tomography (CT) device, and a magnetic resonance imaging (MRI) device.

24. The quality control system according to claim 14, wherein said histories of evaluation results are multiple data entries over time.

25. A quality control system, for one or more medical diagnostic apparatuses, comprising:
   one or more medical diagnostic apparatuses, wherein at least one of said one or more medical diagnostic apparatuses automatically outputs information relating to image quality of at least one of said one or more medical diagnostic apparatuses;
   a device for storing information relating to the image quality of said one or more medical diagnostic apparatuses; and
   a network onto which said one or more medical diagnostic apparatuses and said device are connected.

26. The quality control system according to claim 25, wherein said image quality includes at least one of sensitivity, granularity, root mean square (RMS), detective quantum efficiency (DQE), brightness characteristic of a soft copy display device and resolution characteristic of the soft copy display device.

27. The quality control system according to claim 25, wherein said at least one of said one or more medical diagnostic apparatuses comprises a local memory, said local memory outputting said information relating to image quality of at least one of said one or more medical diagnostic apparatuses during said automatic outputting operation.

28. A quality control system for medical diagnostic apparatuses, comprising:
   a plurality of medical diagnostic apparatuses, wherein said plurality of medical apparatuses comprises at least one medical image input device and at least one medical image output device, said at least one medical image input device having a history of evaluation results related to its image quality;
   a control device which stores histories of evaluation results related to image quality of individual medical diagnostic apparatuses, to control the histories thereof centrally; and a network onto which said plurality of medical diagnostic apparatuses and said control device are connected.

29. The quality control system according to claim 28, wherein at least one of said plurality of medical diagnostic apparatuses is said control device.

30. The quality control system according to claim 28, wherein said image quality includes at least one of sensitivity, granularity, root mean square (RMS), detective quantum efficiency (DQE), brightness characteristics of a soft copy display device and resolution characteristic of the soft copy display device.

31. The quality control system according to claim 28, wherein said at least one medical image input device originates an image from a source being imaged using energy conversion to an electrical signal.

32. The quality control system according to claim 28, wherein said at least one medical image input device is selected from one of a computerized radiography (CR) device, a computerized tomography (CT) device, and a magnetic resonance imaging (MRI) device.

33. The quality control system according to claim 28, wherein said histories of evaluation results are multiple data entries over time.

34. A quality control system for medical diagnostic apparatuses, comprising:

a plurality of medical diagnostic apparatuses, wherein at least one of said plurality of medical diagnostic apparatuses automatically outputs a history of evaluation results on specified items regarding image quality of at least one of said plurality of medical diagnostic apparatuses, to a control device;

said control device stores all histories of evaluation results on specified items regarding image quality of individual medical diagnostic apparatuses, to control the histories thereof centrally; and a network onto which said plurality of medical diagnostic apparatuses and said control device are connected.

35. The quality control system according to claim 34, wherein said image quality includes at least one of sensitivity, granularity, root mean square (RMS), detective quantum efficiency (DQE), brightness characteristic of a soft copy display device and resolution characteristic of the soft copy display device.

36. The quality control system according to claim 34, wherein at least one of said plurality of medical diagnostic apparatuses comprises a local memory, said local memory outputting said information relating to image quality of at least one of said plurality of medical diagnostic apparatuses during said automatic outputting operation.

37. The quality control system according to claim 34, wherein said histories of evaluation results are multiple data entries over time.

* * * * *